(12) United States Patent
Pudil et al.

(10) Patent No.: US 11,607,669 B2
(45) Date of Patent: Mar. 21, 2023

(54) PRECISION RECHARGING BASED ON SORBENT MODULE MANUFACTURING CHARACTERISTICS

(71) Applicant: Medtronic, Inc., Minneapolis, MN (US)

(72) Inventors: Bryant J. Pudil, Plymouth, MN (US); Martin T. Gerber, Maple Grove, MN (US); Christopher M. Hobot, Rogers, MN (US)

(73) Assignee: Medtronic, Inc., Minneapolis, MN (US)

(*) Notice: Subject to any disclaimer, the term of this patent is extended or adjusted under 35 U.S.C. 154(b) by 408 days.

(21) Appl. No.: 16/691,924

(22) Filed: Nov. 22, 2019

(65) Prior Publication Data

US 2020/0261888 A1 Aug. 20, 2020

Related U.S. Application Data

(60) Provisional application No. 62/808,237, filed on Feb. 20, 2019.

(51) Int. Cl.
  *B01J 20/34* (2006.01)
  *B01J 20/02* (2006.01)
  *A61M 1/16* (2006.01)

(52) U.S. Cl.
  CPC ........ *B01J 20/3475* (2013.01); *A61M 1/1696* (2013.01); *B01J 20/0211* (2013.01)

(58) Field of Classification Search
  CPC ........ A61M 1/1696; A61M 2205/3379; A61M 2205/50; A61M 2205/6018; B01D 15/203; B01J 20/0211; B01J 20/0292; B01J 20/08; B01J 20/3475
  See application file for complete search history.

(56) References Cited

U.S. PATENT DOCUMENTS

| | | | |
|---|---|---|---|
| 1,617,288 A | 2/1927 | Kenney |
| 2,703,313 A | 1/1950 | Gill |
| 3,608,729 A | 9/1971 | Haselden |
| 3,617,558 A | 11/1971 | Jones |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,661,246 A | 4/1987 | Ash |

(Continued)

FOREIGN PATENT DOCUMENTS

| CN | 106413878 A | 2/2017 |
|---|---|---|
| EP | 3546042 | 10/2019 |

(Continued)

OTHER PUBLICATIONS

European Search Report for App. No. 20164524.9, dated Aug. 21, 2020.

(Continued)

*Primary Examiner* — Dirk R Bass
(74) *Attorney, Agent, or Firm* — Roger Hahn; Hahn & Associates

(57) ABSTRACT

The invention relates to devices, systems, and methods for precision recharging of sorbent materials in a sorbent module. The devices, systems, and methods use manufacturing characteristics of the sorbent module to set recharge parameters used in recharging the sorbent material.

7 Claims, 3 Drawing Sheets

(56) References Cited

U.S. PATENT DOCUMENTS

| | | |
|---|---|---|
| 5,442,969 A | 8/1995 | Troutner |
| 2002/0016550 A1 | 2/2002 | Sweeney |
| 2003/0097086 A1 | 5/2003 | Gura |
| 2003/0187479 A1 | 10/2003 | Thong |
| 2005/0101901 A1 | 5/2005 | Gura |
| 2005/0234354 A1 | 10/2005 | Rowlandson |
| 2005/0274658 A1 | 12/2005 | Rosenbaum |
| 2006/0037483 A1 | 2/2006 | Kief |
| 2008/0241031 A1 | 10/2008 | Li |
| 2009/0101552 A1 | 4/2009 | Fulkerson |
| 2010/0312172 A1 | 12/2010 | Hoffman |
| 2011/0048949 A1 | 3/2011 | Ding |
| 2012/0095402 A1 | 4/2012 | Lande |
| 2012/0303079 A1 | 11/2012 | Mahajan |
| 2013/0030356 A1 | 1/2013 | Ding |
| 2013/0116578 A1 | 5/2013 | An |
| 2013/0213890 A1 | 8/2013 | Kelly |
| 2014/0336568 A1 | 11/2014 | Wong |
| 2015/0108069 A1 | 4/2015 | Merchant |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243299 A1 | 8/2016 | Gerber |
| 2016/0243540 A1 | 8/2016 | Menon |
| 2016/0243541 A1 | 8/2016 | Menon |
| 2017/0087533 A1 | 3/2017 | Hobot |
| 2018/0221852 A1 | 8/2018 | Pudil |

FOREIGN PATENT DOCUMENTS

| | | |
|---|---|---|
| EP | 3626280 | 3/2020 |
| WO | WO2014121238 A1 | 2/2013 |
| WO | WO 2016/191041 | 12/2016 |

OTHER PUBLICATIONS

Chinese Office Action for App. No. 201810580243.5, dated Jul. 3, 2020.

Chinese Office Action for App. No. 201711179528.X, dated Jul. 27, 2020.

European Search Report for App. No. 20158130.3, dated Jul. 8, 2020.

PRECISION RECHARGING BASED ON SORBENT MODULE MANUFACTURING CHARACTERISTICS

CROSS-REFERENCE TO RELATED APPLICATION

This application claims the benefit of and priority to U.S. Provisional Patent Application No. 62/808,237 filed Feb. 20, 2019, the entire disclosure of which is incorporated by reference herein.

FIELD OF THE INVENTION

The invention relates to devices, systems, and methods for precision recharging of sorbent materials in a sorbent module. The devices, systems, and methods use manufacturing characteristics of the sorbent module to set recharge parameters used in recharging the sorbent material.

BACKGROUND

Zirconium phosphate and zirconium oxide are common sorbent materials used in sorbent dialysis. The zirconium phosphate removes cations, such as potassium, calcium, magnesium, and ammonium ions from spent dialysate. Zirconium oxide removes anions, such as phosphate or fluoride anions from spent dialysate. After use, the zirconium phosphate and zirconium oxide can be reprocessed or recharged to restore a functional capacity or a range of functional capacity of the sorbent materials.

Certain characteristics of zirconium phosphate, zirconium oxide, and other sorbent materials related to the manufacturing process can influence the amount of recharge solutions necessary to restore the functional capacity of the sorbent modules. However, known systems and methods do not take into account manufacturing characteristics to set parameters used in recharging the sorbent materials. Known systems and methods generally set the recharge process based on conservative estimates or worst-case scenario estimates for manufacturing characteristics of the sorbent materials, resulting in higher volumes of recharge solution used, increased costs, more time-consuming processes, and waste.

Hence, there is a need for precision sorbent material recharging systems and methods that use actual values for manufacturing characteristics of the sorbent materials. The need extends to performing precision sorbent recharging accurately, efficiently, and economically. The need includes systems and methods that allow for such precision recharging without the need for excess chemicals or time.

SUMMARY OF THE INVENTION

The first aspect of the invention relates to a system. In any embodiment, the system can comprise a sorbent recharger comprising a recharging flow path that is fluidly connectable to a sorbent module containing at least one sorbent material; at least one recharge solution source containing at least one recharge solution for recharging the at least one sorbent material within the sorbent module, the at least one recharge solution source fluidly connectable to a sorbent module inlet; at least one pump in the recharging flow path for providing recharge solution to the sorbent module; and a processor programmed to set at least one recharge parameter for recharging of the at least one sorbent material based on one or more manufacturing characteristics of the sorbent material contained in the sorbent module.

In any embodiment, the at least one sorbent material can comprise zirconium phosphate.

In any embodiment, the at least one sorbent material can comprise zirconium oxide.

In any embodiment, the one or more manufacturing characteristics can include at least one of: urease activity, urease amount, zirconium phosphate capacity, zirconium phosphate mass, zirconium phosphate particle size, zirconium phosphate loss on drying, alumina mass, and combinations thereof.

In any embodiment, the one or more manufacturing characteristics can include at least one of: zirconium phosphate mass, phosphate bleed rate, zirconium oxide mass, zirconium oxide capacity, zirconium oxide particle size, zirconium oxide loss on drying, alumina mass, urease activity, urease amount, and combinations thereof.

In any embodiment, the at least one recharge parameter can comprise at least one of: time of recharging, recharge temperature, volume of at least one recharge solution, concentration of at least one recharge solution, and combinations thereof.

In any embodiment, the system can comprise a reader in communication with the processor, the reader receiving at least one manufacturing characteristic from a readable component on or in the sorbent module.

The features disclosed as being part of the first aspect of the invention can be in the first aspect of the invention, either alone or in combination, or follow a preferred arrangement of one or more of the described elements.

The second aspect of the invention is drawn to a method. In any embodiment, the method can comprise the steps of introducing at least one recharge solution into a sorbent module containing at least one sorbent material in a sorbent recharger; wherein at least one recharge parameter used when introducing the at least one recharge solution is set based on one or more manufacturing characteristics of the sorbent module containing the at least one sorbent material.

In any embodiment, the sorbent module can contain zirconium phosphate.

In any embodiment, sorbent module can contain zirconium oxide.

In any embodiment, the one or more manufacturing characteristics can include at least one of: urease activity, urease amount, zirconium phosphate capacity, zirconium phosphate mass, zirconium phosphate particle size, zirconium phosphate loss on drying, and alumina mass.

In any embodiment, the one or more manufacturing characteristics can include at least one of: zirconium phosphate mass, phosphate bleed rate, zirconium oxide mass, zirconium oxide capacity, zirconium oxide particle size, urease activity, urease amount, and alumina mass.

In any embodiment, the at least one recharge parameter can comprise at least one of: time of recharging, recharge temperature, volume of at least one recharge solution, and concentration of at least one recharge solution.

The features disclosed as being part of the second aspect of the invention can be in the second aspect of the invention, either alone or in combination, or follow a preferred arrangement of one or more of the described elements.

The third aspect of the invention is drawn to a method. In any embodiment, the method can comprise the step of setting at least one recharge parameter for recharging a sorbent material in a sorbent module; wherein the at least one recharge parameter is set based on one or more manufacturing characteristics of the sorbent module.

In any embodiment, the sorbent module can contain zirconium phosphate.

In any embodiment, the sorbent module can contain zirconium oxide.

In any embodiment, the one or more manufacturing characteristics can include at least one of: urease activity, urease amount, zirconium phosphate capacity, zirconium phosphate mass, zirconium phosphate particle size, zirconium phosphate loss on drying, alumina mass, and combinations thereof.

In any embodiment, the one or more manufacturing characteristics can include at least one of: zirconium phosphate mass, phosphate bleed rate, zirconium oxide mass, zirconium oxide capacity, zirconium oxide particle size, alumina mass, urease activity, urease amount, and combinations thereof.

In any embodiment, the method can comprise the step of introducing at least one recharge solution into the sorbent module with the at least one recharge parameter.

In any embodiment, the at least one recharge parameter can comprise at least one of: time of recharging, recharge temperature, volume of at least one recharge solution, concentration of at least one recharge solution, and combinations thereof.

The features disclosed as being part of the third aspect of the invention can be in the third aspect of the invention, either alone or in combination, or follow a preferred arrangement of one or more of the described elements.

DETAILED DESCRIPTION OF THE INVENTION

Figure 1:
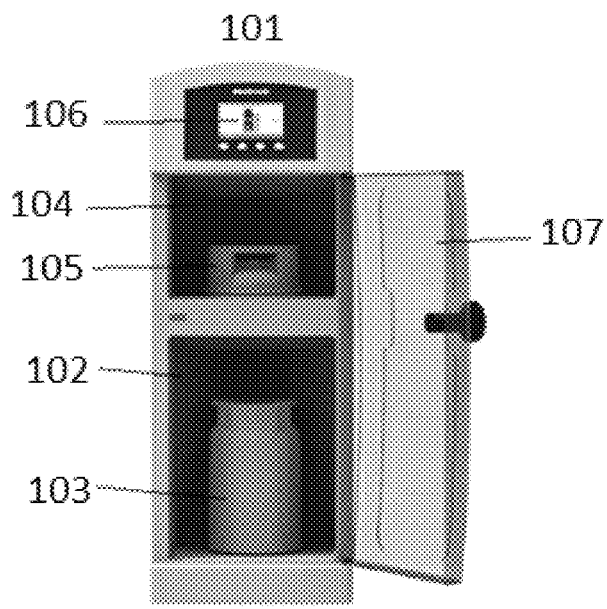
FIG. 1 shows a sorbent recharger for recharging a sorbent material in a sorbent module.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

"Alumina mass" refers to the mass of alumina material within a component.

The phrase "based on" can refer to using information or data obtained by any means wherein the use can be of any form including performing calculations of determined or observed parameters, determining values, transmitting determined or observed values, measuring values, or processing the obtained information or data in any fashion known to those of skill in the art. For example, the phrase "based on data" can refer to performing a calculation or determining one or more value or variable using data.

The terms "contain," "to contain," and "containing" when used in reference to a material refers to retaining that material as contents of a compartment, module, device, or structure.

The term "comprising" includes, but is not limited to, whatever follows the word "comprising." Use of the term indicates the listed elements are required or mandatory but that other elements are optional and may be present.

The term "concentration" refers to an amount of a solute dissolved in a given unit of solvent.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "fluidly connectable" refers to a capability for providing for the passage of fluid, gas, or combination thereof, from one point to another point. The capability of providing such passage can be any connection, fastening, or forming between two points to permit the flow of fluid, gas, or combinations thereof. The two points can be within or between any one or more of compartments of any type, modules, systems, components, such as rechargers, as described herein.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

The terms "introducing," "introduced," or to "introduce" refers to directionally moving or flowing a fluid, a gas, or a combination thereof by any means known to those of skill in the art.

A "manufacturing characteristic" is any variable, either controllable or uncontrollable, for a material or component that is determined at the time the material or component is manufactured that has an impact on the performance of the material or component.

"Phosphate bleed rate" refers to the rate at which phosphate ions are released from a zirconium phosphate material as fluid flows through the material.

"Precision recharging" refers to recharging a sorbent material to a desired state without the need for excess chemicals or solutions. The precision recharging can include using input data or parameters to determine the precise need or amount of chemicals or solutions, temperature, and length of time required to perform sorbent recharging without unnecessary energy consumption or waste generation.

The term "processor" as used is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "programmed," when referring to a processor, can mean a series of instructions that cause a processor to perform certain steps. For example, a processor can be "programmed" to set functions, parameters, variables, or instructions.

The term "pump" refers to any device that causes the movement of fluids or gases by applying suction or pressure.

A "readable component" is any component that can contain information obtainable from a reader.

A "reader" is any component that can obtain information from a second component, such as a barcode or RFID component.

The terms "receiving," "to receive," or "received" in the context of data refers to obtaining information or any other means of data transmission or representation from any source by any means including direct electrical contact, induction, magnetic, wireless transmission, or networked connection.

A "recharge parameter" is any factor or variable used in recharging of a material. In certain embodiments, a recharge parameter can include one or more of a flow rate, concentration, or volume of recharge solutions used in recharging. Other non-limiting examples of a recharge parameter can be time of recharging, recharge temperature, volume of at least one recharge solution, concentration of at least one recharge solution, and combinations thereof.

A "recharge solution" or "recharge solutions" can be a solution containing appropriate ions for recharging a specific sorbent material. A recharge solution can be a single solution containing all necessary ions for recharging a sorbent material. Alternatively, the recharge solution can contain some of the ions for recharging the sorbent material, and one or more other recharge solutions can be used to form a composite "recharge solution" to recharge the sorbent material, as described herein.

A "recharge solution source" can be any fluid or concentrate source from which a recharge solution can be stored, obtained, or delivered therefrom.

"Recharging" refers to treating a sorbent material to restore a functional capacity of the sorbent material putting the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

A "recharging flow path" can be a path through which fluid can travel while recharging a sorbent material in a sorbent module.

The term "recharge temperature" refers to the temperature of one or more components used in recharging a sorbent material. The recharge temperature can refer to a temperature of one or more recharge solutions introduced through a sorbent module containing the sorbent material, or can refer to a temperature of the sorbent material itself.

The term "setting," "set," or "to set" in the context of performing a series of instructions or steps refers to the process of adjusting or controlling one or more variable to a desired value for use in a process, method, or system.

A "sorbent cartridge module" or "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain one or more selected material for use in sorbent dialysis and may or may not contain a "sorbent material" or adsorbent, and less than a full complement of one or more sorbent material needed for performing a sorbent function. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

"Sorbent materials" are materials capable of removing specific solutes from solution, such as cations or anions.

The term "sorbent module inlet" can refer to a portion of a sorbent module through which fluid, gas, or a combination thereof can be drawn into the sorbent module.

The term "sorbent module outlet" can refer to a portion of a sorbent module through which fluid, gas, or a combination thereof can flow or be drawn out of the sorbent module.

A "sorbent recharger" or "recharger" is an apparatus designed to recharge at least one sorbent material, and optionally one or more non-sorbent material.

The term "time of recharging" refers to the total amount of time required to restore the functional capacity of a sorbent material for a given set of recharge parameters.

"Urease amount" refers to the amount of urease physically present in a component. The urease amount can be measured in the number of urease molecules, such as a number of moles, or a mass of urease.

"Urease activity" refers to the ability of a given amount of urease to catalyze the decomposition of urea. One international enzyme unit can liberate 1.0 µmole of NH4 from urea per min at pH 7.0 at 25° C.

The term "volume" refers to the three dimensional space occupied by a substance or container.

"Zirconium oxide" is a sorbent material that removes anions from a fluid, exchanging the removed anions for different anions. Zirconium oxide can also be formed as hydrous zirconium oxide.

"Zirconium oxide capacity" is a measurement of the amount of anions that can be adsorbed by a given amount of zirconium oxide.

"Zirconium oxide loss on drying" refers to the mass change of a given sample of zirconium oxide when heated to an elevated temperature and held for a given period of time. Loss on drying can be measured by storing a sample of zirconium oxide at 110±5° C. for 360±5 minutes and calculating the weight change per gram of sample.

"Zirconium oxide mass" refers to the mass of zirconium oxide within a component.

"Zirconium oxide particle size" refers to the diameter of one or more zirconium oxide particles. In certain embodiments, the zirconium oxide particle size can refer to an average size for a given sample of zirconium oxide. In general, particle size can be specified in terms of D50 (the median particle size), D10 ($10^{th}$ percentile) and D90 ($90^{th}$ percentile).

"Zirconium phosphate" is a sorbent material that removes cations from a fluid, exchanging the removed cations for different cations.

"Zirconium phosphate loss on drying" refers to the mass change of a given sample of zirconium oxide when heated to an elevated temperature and held for a given period of time. Loss on drying can be measured by storing a sample of zirconium phosphate at 110±5° C. for 240±5 minutes and calculating the weight change per gram of sample.

"Zirconium phosphate capacity" is a measurement of the amount of cations that can be adsorbed by a given amount of zirconium phosphate.

"Zirconium phosphate mass" refers to the mass of zirconium phosphate within a component.

"Zirconium phosphate particle size" refers to the diameter of one or more zirconium phosphate particles. In certain embodiments, the zirconium phosphate particle size can refer to an average size for a given sample of zirconium phosphate. Particle size can be also specified in terms of D50 (the median particle size), D10 ($10^{th}$ percentile) and D90 ($90^{th}$ percentile).

Precision Recharging

The invention is drawn to systems and methods that can provide for precision recharging of a sorbent material within a sorbent module that is not limited to any particular standard but can be dependent upon input variables to achieve a desired state. Precision recharging is an approach for recharging a sorbent material that takes into account manufacturing characteristics, individual variability of the sorbent cartridge, state of materials, and conditions being used to recharge the sorbent material. Precision recharging can reflect the implied effects from a particular dialysis and recharging setup as well as the specific conditions for a particular recharging setup, and the types and quantities of materials and fluids used for sorbent material recharging. Precision recharging can provide for more accurate, effective, and/or economical recharging of a sorbent material. The approach is contrasted to a one-size-fits-all approach, in which sorbent material recharging relies on averages without any consideration of specific conditions, features, and factors, or any other variable that might have an impact on sorbent recharging.

FIG. 1 illustrates a non-limiting embodiment of a sorbent recharger 101 for recharging zirconium phosphate in a zirconium phosphate sorbent module 103 and/or zirconium oxide in a zirconium oxide sorbent module 105. The sorbent recharger 101 can include a receiving compartment 102 for receiving a zirconium phosphate sorbent module 103. Fluid connections (not shown in FIG. 1) connect to the top and bottom of the zirconium phosphate sorbent module 103 for introducing recharge solutions into, through and out of the zirconium phosphate sorbent module 103. The recharge solutions replace ions bound to the sorbent materials during dialysis with new ions, recharging the zirconium phosphate within the zirconium phosphate sorbent module 103 and/or zirconium oxide in a zirconium oxide sorbent module 105, allowing reuse of the sorbent modules 103 and 105 in dialysis. The sorbent recharger 101 can include a second receiving compartment 104 for receiving a second sorbent module, such as zirconium oxide sorbent module 105, which is also fluidly connected to recharge solution sources for recharging of zirconium oxide sorbent module 105. The sorbent recharger 101 can include any number of receiving compartments for receiving any number of zirconium phosphate and/or zirconium oxide sorbent modules. In certain embodiments, a sorbent recharger can recharge only a single sorbent material, such as a sorbent recharger with one or more receiving compartments each for receiving sorbent modules containing the same sorbent materials. Alternatively, the sorbent recharger 101 can include multiple receiving compartments for receiving sorbent modules containing different sorbent materials, as illustrated in FIG. 1. A user interface 106 can be provided to start or control the recharging process by the user and to receive information from the sorbent recharger 101, such as the volume of one or more recharge solutions necessary for recharging. The user interface 106 can also provide the status of the recharging process to the user, such as the time to completion for each recharging step, or a time to complete the entire recharging process. User interface 106 provides alert messages if any problems are detected during recharging, such as leaks, occlusions, pump failures, or mismatched chemicals. The user interface 106 can also allow the user to input information into the sorbent recharger 101, such as one or more manufacturing characteristics of the sorbent modules 103 and 105. A door 107 on the sorbent recharger 101 controls access to the receiving compartments 102 and 104 during operation.

The sorbent recharger 101 can have one or more processors for receiving data concerning one or more manufacturing characteristics of the sorbent modules 103 and 105 and setting one or more recharge parameters, such as a volume of recharge solution, a concentration of recharge solution, or and/or a flow rate of recharge solution necessary for recharging the sorbent modules. The sorbent recharger 101 can transmit data obtained from a sensor wirelessly or by wired connection. The sorbent recharger 101 can be connected to a local area network (LAN) or a secure internet connection that transmits the required instructions or data to a component that either process the data or performs a set of instructions. It will be understood that the determination and setting of the recharge parameters is not limited to a component physically attached to the sorbent recharger 101 or other component local to the dialysis system, but can be performed at any local or remote data center including cloud infrastructure, or other network of remote servers hosted on the Internet that can store, manage, and process data. The networked systems can be secured by any known methods and procedures as known to those of skill in the art. Although illustrated in FIG. 1 as having two receiving compartments 102 and 104, a sorbent recharger for recharging a single sorbent material can have a single receiving compartment or multiple receiving compartments for receiving and recharging multiple modules containing the same sorbent material. Sorbent rechargers with any number of receiving compartments for recharging any number or combination of zirconium oxide and/or zirconium phosphate sorbent modules can be constructed. For example, a sorbent recharger with two zirconium phosphate receiving compartments and two zirconium oxide receiving compartments can be similarly constructed. The sorbent rechargers can have 1, 2, 3, 4, 5, 6, or more receiving compartments, each capable of receiving zirconium oxide or zirconium phosphate sorbent modules.

Figure 2:
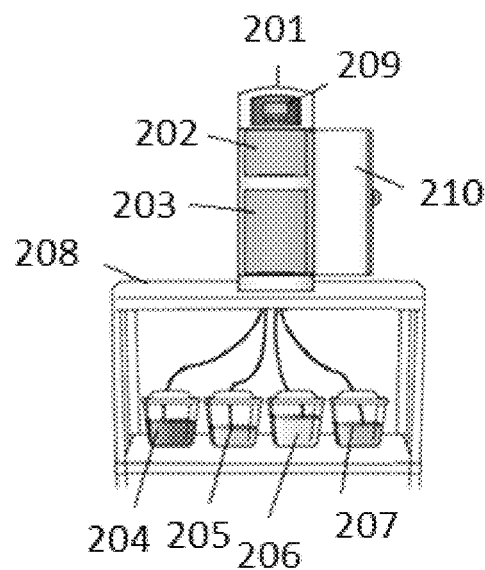
FIG. 2 shows a sorbent recharger connected to recharge solution sources for recharging sorbent materials.

FIG. 2 illustrates a non-limiting embodiment of a sorbent recharger 201 set up for recharging zirconium phosphate and/or zirconium oxide. To recharge the zirconium phosphate and/or zirconium oxide, one or more recharge solutions can be passed through a zirconium phosphate sorbent module. As shown in FIG. 2, the sorbent recharger 201 can be fluidly connected to one or more recharge solution sources, such as water source 204, brine source 205, base source 206, and disinfectant source 207. The brine source 205 can contain a brine solution having a sodium salt and buffer. As an alternative, separate sodium and buffer sources can be used, or the buffer can be replaced by separate acid and base sources. Any number of recharge solution sources can be included. The sorbent recharger 201 has a zirconium phosphate receiving compartment 203 and/or a zirconium oxide receiving compartment 202. As described, the sorbent recharger 201 can include any number of receiving compartments for receiving any combination of zirconium oxide and zirconium phosphate sorbent modules. The sorbent recharger 201 can also include one or more pumps and valves (not shown in FIG. 2) for selectively introducing the recharge solutions from the recharge solution sources to the sorbent modules. As shown in FIG. 2, the recharge solution sources are housed external to the sorbent recharger 201. Alternatively, the recharge solution sources can be housed within the sorbent recharger 201. A drain line (not shown) can be connected to the sorbent recharger 201 for disposal of waste fluids exiting the sorbent modules. The drain line can be fluidly connected to a drain, or alternatively, the drain line can be fluidly connected to one or more waste reservoirs for storage and later disposal. As illustrated in FIG. 2, the sorbent recharger 201 can be small enough to fit on top of a table 208. However, larger sorbent rechargers can be used. A user interface 209 can allow user control of the recharging process and provide messages concerning the recharging. Door 210 controls access to the receiving compartments 202 and 203 during recharging.

Figure 3:
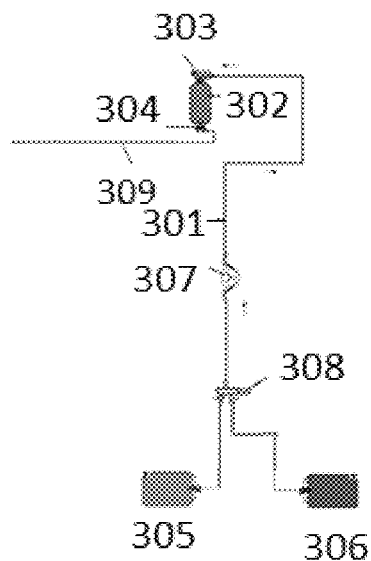
FIG. 3 shows a zirconium phosphate recharging flow path.

The sorbent rechargers can include one or more recharging flow paths fluidly connected to the sorbent modules. FIG. 3 illustrates a non-limiting embodiment of a zirconium phosphate recharging flow path 301 for recharging zirconium phosphate in a zirconium phosphate sorbent module 302. After dialysis, the zirconium phosphate sorbent module 302 can be removed from the dialysis system and placed in the sorbent recharger. The zirconium phosphate sorbent module 302 can be fluidly connectable to the zirconium phosphate recharging flow path 301 through zirconium phosphate sorbent module inlet 303 and zirconium phosphate sorbent module outlet 304 into effluent line 309. The zirconium phosphate recharging flow path 301 can include at least one pump 307 to provide a driving force for moving fluids through the zirconium phosphate recharging flow path 301. In certain embodiments, two or more pumps can be included for individually introducing fluids from the recharge solution sources into the zirconium phosphate sorbent module 302. As described, the system and methods allow for setting a flow rate of the recharge solutions through the zirconium phosphate recharging flow path 301 for precision recharging. The zirconium phosphate recharging flow path 301 can include one or more recharge solution sources, including a brine source 305 and a water source 306. The brine source 305 can contain a brine solution of a salt, such as sodium chloride, and a buffer, such as a mixture of sodium acetate and acetic acid. The sodium and hydrogen ions in the recharge solution displace the ammonium ions and other cations adsorbed by the zirconium phosphate during a prior dialysis session. Although shown as a single brine source 305, multiple recharge solution sources can be used. For example, a first recharge solution source containing sodium chloride and a second recharge solution source containing an acetate buffer. Alternatively, three recharge solution sources can be used, with sodium chloride, sodium acetate, and acetic acid in separate recharge solution sources. If multiple recharge solution sources are used, the recharge solutions can be mixed within the zirconium phosphate recharging flow path 301 or pumped through the zirconium phosphate sorbent module 302 sequentially. Any combination of sodium salt and buffer capable of causing exchange of ammonium, potassium, calcium, and magnesium for sodium and hydrogen ions can be used as the recharge solutions. The water from water source 306 can be used to dilute the brine solution from brine source 305 if a concentrated brine solution is used, and to rinse the zirconium phosphate sorbent module 302 before and after introducing the brine solution through the zirconium phosphate sorbent module 302. In certain embodiments, the brine source 305 can contain a brine concentrate having a concentration of salt and buffer greater than that to be used in recharging. The brine solution can be diluted in-line with water from the water source 306 to generate a recharge solution with a desired concentration, as described. Optional valve 308 can be included to control the movement of fluid from either the brine source 305 or water source 306. Alternatively, separate pumps on fluid lines fluidly connected to each recharge solution source can be used. A processor (not shown) can be programmed to control the pumps or valves to direct recharge solutions from the recharge solution sources through the zirconium phosphate sorbent module 302 to recharge the zirconium phosphate with specified recharge parameters. The processor can receive one or more manufacturing characteristics of the zirconium phosphate sorbent module 302 and/or other modules used during dialysis and set the recharge parameters used for recharging the zirconium phosphate. In certain embodiments, the manufacturing parameters may also affect an amount of disinfectant solution necessary to disinfect the zirconium phosphate sorbent module 302. However, in other embodiments, the effects of the manufacturing parameters on the amount of disinfectant needed can be small. One of skill in the art will understand that multiple pump and valve arrangements can be used to pump the necessary recharge solutions through the zirconium phosphate sorbent module 302.

During a dialysis session, the zirconium phosphate can remove cations from spent dialysate, including ammonium, potassium, calcium, and magnesium, exchanging the cations for hydrogen and sodium ions. The ammonia is formed by the breakdown of urea by urease in the sorbent cartridge during treatment. The sodium chloride and buffer solutions used in recharging the zirconium phosphate serve to displace the cations absorbed during treatment with sodium and hydrogen ions, facilitating reuse of the zirconium phosphate.

Certain manufacturing characteristics of the zirconium phosphate sorbent module 302 or other sorbent modules used in a dialysis session can cause different amounts of sodium and hydrogen to be needed to recharge the zirconium phosphate, depending on conditions used. For example, urease activity, urease amount, and alumina mass used in a sorbent module containing alumina and urease can influence the requirements for recharging the zirconium phosphate. The urease amount and activity affect a fractional conversion of urea to ammonium. For example, a higher urease amount or a higher urease activity can result in a greater proportion of the urea being converted to ammonium ions, thereby increasing the ammonium load on the zirconium phosphate and increasing a volume of recharge solutions required for recharging. One of skill in the art will understand that the urease amount and activity will not affect the amount of ammonium ions adsorbed by the zirconium phosphate as long as the urea from the patient is fully hydrolyzed. If all of the urea from the patient is fully hydrolyzed with a minimum amount and activity of urease, then increasing the amount or activity of urease will not affect the amount of ammonium ions produced. The urease amount may also affect the amount of calcium and magnesium that are removed before reaching the zirconium phosphate. In certain embodiments, the alumina and urease used in the sorbent cartridge can be included in zirconium phosphate sorbent module 302. Alternatively, an additional sorbent module (not shown) can be included that contains alumina and urease and that can be connected to zirconium phosphate sorbent module 302 to form all or part of a sorbent cartridge. Manufacturing characteristics of the zirconium phosphate sorbent module 302 can also influence the requirements for recharging. Zirconium phosphate capacity, zirconium phosphate mass, zirconium phosphate particle size, and zirconium phosphate loss on drying can each be used in setting the recharge parameters, as described. As a non-limiting example, zirconium phosphate particle size can have an average diameter of 60 microns. The zirconium phosphate loss on drying generally has a minimal impact on the zirconium phosphate capacity. However, if the zirconium phosphate loss on drying is outside of a normal specified range, a lower loss on drying could reduce the zirconium phosphate capacity. The zirconium phosphate mass and capacity will affect the amount of recharge solutions necessary for full recharging only if a minimum capacity of the zirconium phosphate was exceeded during treatment. The minimum possible capacity of the zirconium phosphate can be calculated as described. For any treatment that does not reach the minimum breakthrough capacity of the zirconium phosphate, the zirconium phosphate capacity and mass will have no impact on recharging. Table 1 includes possible manufacturing characteristics and the effect of those characteristics on the zirconium phosphate recharge parameters.

TABLE 1

| Manufacturing Characteristic | Recharge Parameters |
| --- | --- |
| Urease Activity | Positive correlation |
| Urease Amount | Positive correlation |
| Alumina Mass | Weak negative or no correlation |
| Zirconium Phosphate Capacity | Positive correlation |
| Zirconium Phosphate Mass | Positive correlation |
| Zirconium Phosphate Particle Size | Positive or negative correlation |
| Zirconium Phosphate Loss on Drying | No correlation within specification range |

One of skill in the art will understand that there are interdependencies between concentration, time of recharging, volume and flow rate. For example, at a faster flow rate or at a higher recharge solution concentration, recharging the sorbent material may be quicker, but may require additional chemicals. At lower flow rates or recharge solution concentrations the process can be more efficient with respect to chemical usage, but the time of recharging can be longer. As a non-limiting example, for a given set of manufacturing characteristics, recharging may be complete after 60 minutes with 6 L of brine solution at 4 M concentration and 80° C. However, a lower volume may be used if the length of time is increased. A user can input the values that are desired to be minimized based on the user goals, and the system can determine the proper concentration, flow rate, temperature, and/or volume of the recharge solutions to minimize the desired parameters based on the manufacturing characteristics. For example, if the system is used in a clinic where time optimization is a user goal, the user may trade-off volume optimization by using higher flow rates or higher concentrations. If the system is used at home and volume optimization is the user goal, a lower flow rate or concentration of the recharge solutions can be used. The system can be adaptive to the needs of the user, with the user defining the desired objectives or goals for the recharging process, such as to minimize time of recharging or to minimize chemical usage. The user goals can be a variable programmed into the processor to determine the precision recharging parameters. In certain embodiments, the sorbent recharger can use a higher concentration or flow rate at the beginning of recharging, and adjust the concentration and/or flow rate lower as the recharging process nears completion, minimizing both the time of recharging and volume of recharge solutions necessary for recharging the zirconium phosphate.

In certain embodiments, the zirconium phosphate sorbent module 302 can communicate with the processor (not shown) to input the manufacturing characteristics into the system. For example, a readable component, such as an RFID or other tracking component, can be affixed to or embedded in zirconium phosphate sorbent module 302. The readable component can include the manufacturing characteristics of the zirconium phosphate sorbent module 302, as well as other sorbent modules used during dialysis. The sorbent recharger can include a reader that reads the readable component to receive the manufacturing characteristics for a specific sorbent module. Alternatively, a user can manually input the manufacturing characteristics through a user interface on the sorbent recharger. One of skill in the art will understand that the reader or user interface need not be included as part of the sorbent recharger, and can instead be a separate component that can interact with the processor of the sorbent recharger.

Figure 4:
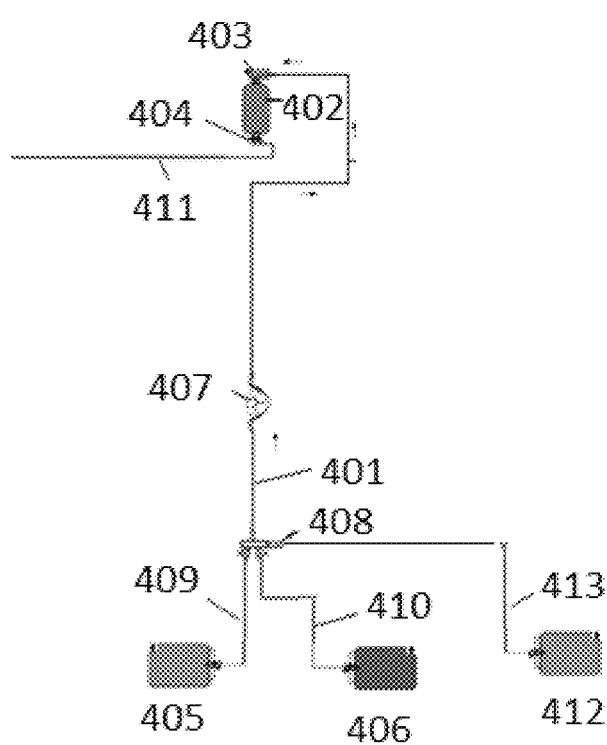
FIG. 4 shows a zirconium oxide recharging flow path.

FIG. 4 illustrates a non-limiting embodiment of a zirconium oxide recharging flow path 401 for recharging zirconium oxide in a zirconium oxide sorbent module 402. After dialysis, the zirconium oxide sorbent module 402 can be removed from the dialysis system and placed in the sorbent recharger. The zirconium oxide sorbent module 402 can be fluidly connectable to the zirconium oxide recharging flow path 401 through zirconium oxide sorbent module inlet 403 and zirconium oxide sorbent module outlet 404 into effluent line 411. The zirconium oxide recharging flow path 401 can include at least one pump 407 to provide a driving force for moving fluids through the zirconium oxide recharging flow path 401. In certain embodiments, two or more pumps can be included for individually introducing fluids from the recharge solution sources into the zirconium oxide sorbent module 402. As described, the system and methods allow for setting a flow rate of the recharge solutions through the zirconium oxide recharging flow path 401 for precision recharging. The zirconium oxide recharging flow path 401 can include one or more recharge solution sources, including a base source 405 fluidly connected to the zirconium oxide recharging flow path 401 through fluid line 409 and optionally a free chlorine source 406 fluidly connected to the zirconium oxide recharging flow path 401 through fluid line 410. The base source 405 can contain a base solution, such as sodium hydroxide or potassium hydroxide. Depending on the concentration and recharge temperature of the base solution, the base solution can also disinfect the zirconium oxide sorbent module 402. Alternatively, a free chlorine solution can be used for disinfection. The free chlorine source 406 can contain any free chlorine solution, including a solution of sodium hypochlorite, potassium hypochlorite or trichloroisocyanuric acid. The hydroxide ions in the base solution displace anions, such as phosphate ions, that have been adsorbed by the zirconium oxide during treatment. Although shown as two separate sources in FIG. 4, a single recharge solution source can be used containing both a base solution and a free chlorine solution. If multiple recharge solution sources are used, the recharge solutions can be mixed within the zirconium oxide recharging flow path 401 or pumped through the zirconium oxide sorbent module 402 sequentially. Water from a water source 412 can be used to dilute the base or free chlorine solution if concentrated solutions are used, and to rinse the zirconium oxide sorbent module 402 before and after introducing the base and free chlorine solutions through the zirconium oxide sorbent module 402 through fluid line 413. Optional valve 408 can be included to control the movement of fluid from r the base source 405, free chlorine source 406, or water source 412. Alternatively, separate pumps on fluid lines fluidly connected to each recharge solution source can be used. A processor (not shown) can be programmed to control the pumps or valves to direct recharge solutions from the recharge solution sources through the zirconium oxide sorbent module 402. One of skill in the art will understand that multiple pump and valve arrangements can be used to introduce the necessary recharge solutions through the zirconium oxide sorbent module 402.

During a dialysis session, the zirconium oxide serves to remove anions from spent dialysate, including phosphate. The hydroxide ions in the base solution displace anions, such as phosphate ions, that have been adsorbed by the zirconium oxide during treatment. The free chlorine acts to disinfect the zirconium oxide sorbent module 402.

Certain manufacturing characteristics of the zirconium oxide sorbent module 402 or other sorbent modules used in a dialysis session can cause different amounts of base to be needed to recharge the zirconium oxide, depending on conditions used. For example, zirconium phosphate mass, phosphate bleed rate from the zirconium phosphate in the sorbent cartridge and alumina mass used in one or more sorbent modules containing zirconium phosphate, alumina and urease can influence the requirements for recharging the zirconium oxide. During treatment a certain amount of phosphate ions will bleed from a sorbent module containing zirconium phosphate. The phosphate ions will be adsorbed by the zirconium oxide, increasing the phosphate load on the zirconium oxide. A higher mass of zirconium phosphate used during treatment will increase the amount of phosphate ions that bleed from the sorbent module containing zirconium phosphate. Generally, the phosphate bleed rate can be about 4,000-mg of phosphate per kg of zirconium phosphate; however, one of ordinary skill will understand that other phosphate bleed rates are possible. The alumina and urease in a sorbent module containing alumina and urease can remove phosphate and fluoride ions from the dialysate. A higher amount of alumina and/or urease can decrease the amount of fluoride and phosphate ions reaching the zirconium oxide, reducing the zirconium oxide utilization and resulting in a reduced volume of recharge solutions necessary to recharge the zirconium oxide. In certain embodiments, the zirconium phosphate, alumina and urease used in the sorbent cartridge can be included in zirconium oxide sorbent module 402. Alternatively, one or more additional sorbent modules (not shown) can be included that contain zirconium phosphate, alumina and urease and that can be connected to zirconium oxide sorbent module 402 to form all or part of a sorbent cartridge. Manufacturing characteristics of the zirconium oxide sorbent module 402 can also influence the requirements for recharging. Zirconium oxide mass, zirconium oxide capacity, zirconium oxide particle size, and zirconium oxide loss on drying can each be used in setting the recharge parameters, as described. Generally, the zirconium oxide capacity will be about 1-mmol phosphate ions per gram of zirconium oxide. However, if the capacity is higher or lower, the recharge parameters can be adjusted accordingly. The average particle size of the zirconium oxide is about a diameter of 20 microns. The zirconium oxide loss on drying generally has a minimal impact on the zirconium oxide capacity. However, if the zirconium oxide loss on drying is outside of a normal specified range, a lower loss on drying could reduce the zirconium oxide capacity. Table 2 includes possible manufacturing characteristics and the effect of those characteristics on the zirconium oxide recharge parameters.

TABLE 2

| Manufacturing Characteristic | Recharge Parameters |
| --- | --- |
| Phosphate Bleed Rate | Positive correlation |
| Zirconium Phosphate Mass | Positive correlation |
| Alumina Mass | Negative correlation |
| Urease Amount | Negative correlation |
| Urease Activity | Negative correlation |
| Urease Activity and Amount | Negative correlation |
| Zirconium Oxide Capacity | Positive correlation |
| Zirconium Oxide Mass | Positive correlation |
| Zirconium Oxide Particle Size | Positive or negative correlation |
| Zirconium Oxide Loss on Drying | No correlation within specification range |

As described, there are interdependencies between concentration, time of recharging, volume and flow rate. The user can input the values that are desired to be minimized based on the user goals, and the system can determine the proper concentration, flow rate, temperature, and/or volume of the recharge solutions to minimize the desired parameters based on the manufacturing characteristics.

Figure 5:
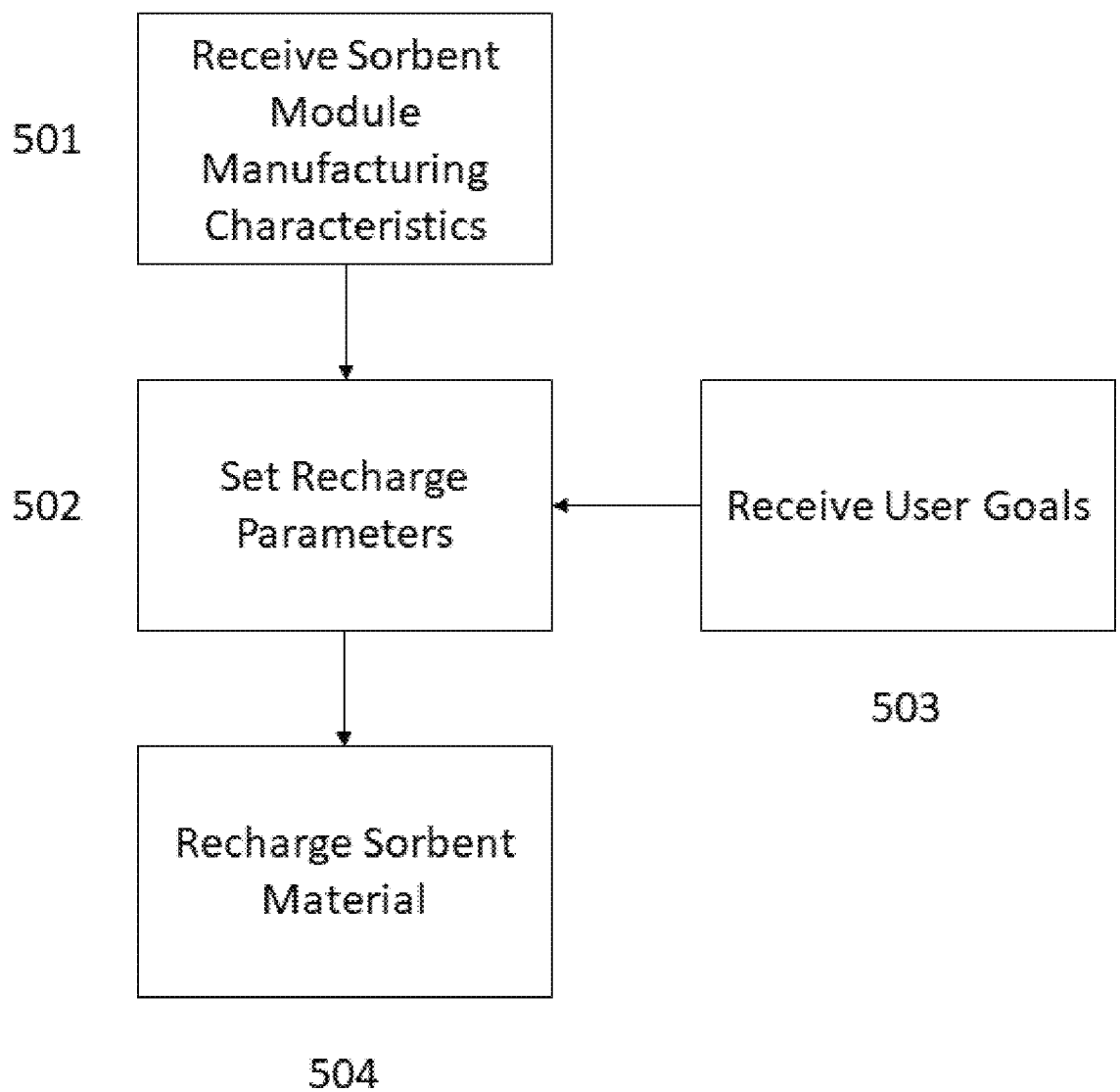
FIG. 5 is a flow chart showing a method for precision recharging of a sorbent material based on sorbent module manufacturing characteristics.

FIG. 5 is a flow chart for performing precision recharging based on one or more manufacturing characteristics of the sorbent module. The sorbent module used in the method of FIG. 5 can contain either zirconium phosphate or zirconium oxide. In step 501, the system can receive one or more manufacturing characteristics for the sorbent module. As described, the manufacturing characteristics can depend on whether the sorbent module contains zirconium phosphate or zirconium oxide.

The processor can receive the manufacturing characteristics for the sorbent module containing the sorbent material to be recharged and/or any other sorbent modules used in a dialysis session from any source. In certain embodiments, a readable component, such as an RFID tag or bar code, can be affixed to or embedded in the sorbent modules, and automatically read by a reader in communication with the processor, including prior to dialysis, after dialysis, prior to recharging, and after recharging. The reader can track the sorbent modules and manufacturing characteristics that affect the amount of recharge solutions necessary to recharge the sorbent modules. The manufacturing characteristics can be communicated to the processor, which can then determine the amount of recharge solution necessary through mathematical algorithms, look-up tables or a combination thereof. Alternatively, a user can enter the manufacturing characteristics through a user interface in communication with the processor, with the manufacturing characteristics provided to the user by the manufacturer. In certain embodiments, periodic inspections of the sorbent modules can be made to test the manufacturing characteristics for a given lot of sorbent modules.

Optionally, in step 503, user goals can be received by the system. As described, the user can request that the recharging take a certain amount of time, use a certain amount of chemicals, or occur at a certain temperature. In step 502, the system can set the recharge parameters based on the manufacturing characteristics, and optionally the user goals, such as to minimize time of recharging, chemicals, or any other factors. In step 504, the system can introduce the recharge solutions into and through the sorbent module using the recharge parameters set in step 502 to recharge the sorbent material inside the sorbent module.

The processor can set the recharge parameters using any method known in the art, including lookup tables, mathematical algorithms, or a combination thereof. For example, the processor can use a lookup table to determine the proper recharge parameters based on a given particle size for zirconium phosphate or zirconium oxide, along with any other manufacturing characteristics received by the processor. The processor can also use lookup tables or mathematical algorithms to adjust one or more recharge parameters based on user goals, as described. For example, if a user wishes to minimize the amount of brine solution used in recharging zirconium phosphate, the processor can then set a lower flow rate and brine concentration and a higher recharge temperature based on the lookup tables.

The processor can also use mathematical algorithms to set the recharge parameters. The amount of recharge chemicals needed is equal to the capacity of the sorbent material minus the amount of ions adsorbed by the sorbent material times a constant. The constant is based on the manufacturing characteristics and the recharge parameters used and can be obtained by the processor to set the recharge process.

As a non-limiting example, Table 3 illustrates capacity of various lots of zirconium phosphate. The capacity can be measured by the supplier or experimentally derived, and is given in mg of $NH_4$/gram of zirconium phosphate. As described, the capacity of the zirconium phosphate in each sorbent module can be tracked using a readable component affixed to or embedded in the sorbent module. One of skill in the art will understand that the lot numbers are for identification purposes only.

TABLE 3

| Lot | Capacity (mg $NH_4$/gram zirconium phosphate) |
| --- | --- |
| 40059 | 19.8 |
| 40060 | 19.4 |
| 40062 | 19.3 |
| 40063-1 | 21.8 |
| 40063-2 | 20.0 |
| 40064-1 | 21.8 |
| 40064-2 | 21.6 |
| 40066 | 22.1 |
| Average | 20.8 |
| Standard deviation | 1.13 |
| $99^{th}$% UL | 24.2 |

As shown in Table 3, the average capacity of the zirconium phosphate is 20.8 mg $NH_4$/gram zirconium phosphate. The standard deviation is 1.13 mg $NH_4$/gram zirconium phosphate, meaning that the $99^{th}$ percentile upper limit is 24.2 mg $NH_4$/gram zirconium phosphate. That is, the maximum capacity extended is 24.2 mg $NH_4$/gram zirconium phosphate.

As a non-limiting example, the mass of zirconium phosphate in each sorbent module can be 2700 grams±1.5%, meaning the maximum mass expected is 2741 grams of zirconium phosphate in each sorbent module. The maximum expected total capacity of each zirconium phosphate sorbent module will be 24.2 mg $NH_4$/gram zirconium phosphate*2741 g zirconium phosphate, or 66,246 mg $NH_4$. EQ(1) provides an adjustment to the recharge volume based on the actual mass and capacity.

$$ZP\ mass\ (g) * ZP\ capacity\ (mg\ NH_4/gram\ zirconium\ phosphate)/66{,}246\ mg\ NH4 = F \quad \text{EQ(1)}$$

Where the ZP mass and the ZP capacity are the actual mass and capacity of zirconium phosphate in the sorbent module, and F is an adjustment factor for the recharge process. To estimate the volume or amount of recharge solution needed, one of ordinary skill can multiply an amount of recharge solutions that would be used with a maximum expected mass and capacity by the adjustment factor F.

In certain embodiments, the amount of recharge solutions necessary to recharge a sorbent module containing the maximum expected mass and capacity can be obtained for a given set of recharge parameters, such as flow rate, temperature, and concentration of the recharge solutions. At the same flow rate, temperature, and concentration, the actual amount of the recharge solution necessary can be the maximum amount times the adjustment factor F. The processor can use a lookup table to determine the amount of recharge solution necessary with desired recharge parameters based on the user goals, and can determine the volume of recharge solution necessary for a specific zirconium phosphate sorbent module using EQ(1).

In certain embodiments, the processor may have a standard recharge volume based on the average or maximum expected mass and capacity. One of skill in the art can modify EQ(1) to use the average mass and capacity rather than the maximum. The processor can then multiply the standard recharge volume for a given set of recharge parameters by the adjustment factor F to determine the necessary amount of recharge solution for a specified zirconium phosphate sorbent module. Alternatively, the processor can calculate the amount of recharge solution necessary for the maximum or average expected mass and capacity based on patient parameters and/or the dialysate prescription to determine the total amount of ions adsorbed by the zirconium phosphate during treatment, multiplying the calculated amount by the adjustment factor F to calculate the amount of the recharge solutions necessary for a specific zirconium phosphate sorbent module.

One of skill in the art will understand that the same information in Table 3 can be obtained for zirconium oxide rather than zirconium phosphate. The process of obtaining the adjustment factor F and using the adjustment factor to determine the necessary amount of recharge solutions to recharge the zirconium oxide will be the same as that described for zirconium phosphate. Further, similar tables and equations can be used for any one or more of the manufacturing parameters listed in Tables 1-2.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination, or follow a preferred arrangement of one or more of the described elements.

We claim:

1. A system, comprising:
   a sorbent recharger, comprising a recharging flow path that is fluidly connectable to a sorbent module containing at least one sorbent material;
   at least one recharge solution source containing at least one recharge solution for recharging the at least one sorbent material within the sorbent module, the at least one recharge solution source fluidly connectable to a sorbent module inlet;
   at least one pump in the recharging flow path for providing recharge solution to the sorbent module; and
   a processor programmed to set at least one recharge parameter for recharging of the at least one sorbent material based on one or more manufacturing characteristics of the sorbent material contained in the sorbent module;

wherein the one or more manufacturing characteristics of the sorbent material comprise at least a particle size of the sorbent material.

2. The system of claim 1, wherein the recharge solution source contains at least one recharge solution for recharging zirconium phosphate.

3. The system of claim 1, wherein the recharge solution source contains at least one recharge solution for recharging zirconium oxide.

4. The system of claim 2, wherein the one or more manufacturing characteristics further include at least one of: urease activity, urease amount, zirconium phosphate capacity, zirconium phosphate mass, zirconium phosphate loss on drying, alumina mass, and combinations thereof.

5. The system of claim 3, wherein the one or more manufacturing characteristics include at least one of: zirconium phosphate mass, phosphate bleed rate, zirconium oxide mass, zirconium oxide capacity, zirconium oxide loss on drying, alumina mass, urease activity, urease amount, and combinations thereof.

6. The system of claim 1, wherein the at least one recharge parameter comprises at least one of: time of recharging, recharge temperature, volume of at least one recharge solution, concentration of at least one recharge solution, and combinations thereof.

7. The system of claim 1, further comprising a reader in communication with the processor, the reader receiving at least one manufacturing characteristic from a readable component on or in the sorbent module.

* * * * *